(12) United States Patent
Maurer et al.

(10) Patent No.: US 9,139,600 B2
(45) Date of Patent: Sep. 22, 2015

(54) ACETYLENE BRIDGED LINKERS AND METAL-ORGANIC FRAMEWORKS (MOFS) PRODUCED THEREOF

(71) Applicant: BASF SE, Ludwigshafen (DE)

(72) Inventors: Stefan Maurer, Ludwigshafen (DE); Ulrich Müller, Neustadt (DE); Vijay Narayanan Swaminathan, Mumbai (IN); Shrirang Bhikaji Hindalekar, Barivalli (IN); Amal Pandya, Mumbai (IN)

(73) Assignee: BASF SE, Ludwigshafen (DE)

( * ) Notice: Subject to any disclaimer, the term of this patent is extended or adjusted under 35 U.S.C. 154(b) by 112 days.

(21) Appl. No.: 14/030,096

(22) Filed: Sep. 18, 2013

(65) Prior Publication Data

US 2014/0081044 A1 Mar. 20, 2014

(30) Foreign Application Priority Data

Sep. 19, 2012 (IN) .................. 12/003897/CHENP (51) Int. Cl.
| | | |
|---|---|---|
| C07C 65/19 | (2006.01) | |
| C07C 49/84 | (2006.01) | |
| C07C 65/03 | (2006.01) | |
| C07F 3/02 | (2006.01) | |
| C07C 69/94 | (2006.01) | |
| C07F 7/08 | (2006.01) | |
| C07C 69/92 | (2006.01) | |

(52) U.S. Cl.
CPC . *C07F 3/02* (2013.01); *C07C 65/19* (2013.01); *C07C 69/92* (2013.01); *C07C 69/94* (2013.01); *C07F 7/0818* (2013.01)

(58) Field of Classification Search
CPC .......... C07C 65/03; C07C 49/84; C07C 65/19
See application file for complete search history.

(56) References Cited

U.S. PATENT DOCUMENTS

| | | | |
|---|---|---|---|
| 5,185,454 | A | 2/1993 | Bader et al. |
| 6,211,234 | B1 | 4/2001 | Astles et al. |
| 2010/0029476 | A1 | 2/2010 | Trukhan et al. |

FOREIGN PATENT DOCUMENTS

| | | |
|---|---|---|
| CN | 101534947 | 9/2009 |
| DE | 3936297 | 5/1991 |
| EP | 0102544 | 3/1984 |
| EP | 0200260 | 12/1986 |
| EP | 0389041 | 3/1989 |
| EP | 0425930 | 5/1991 |
| EP | 0592050 | 4/1994 |

(Continued)

OTHER PUBLICATIONS

PCT International Search Report in PCT/IB2013/056778, mailed Feb. 6, 2014, 5 pages.

(Continued)

*Primary Examiner* — Rosalynd Keys
*Assistant Examiner* — Jennifer C Sawyer
(74) *Attorney, Agent, or Firm* — Servilla Whitney LLC (57) ABSTRACT

Described are acetylene bridged linkers, metal-organic frameworks produced thereof, processes for producing the linkers and the metal-organic frameworks, and the use of the metal-organic frameworks. The metal-organic frameworks possess an enhanced ability to adsorb and desorb high amounts of gases, in particular methane or hydrogen. The metal-organic frameworks have a high porosity and, thus, a high inner surface.

9 Claims, 5 Drawing Sheets (56) References Cited

FOREIGN PATENT DOCUMENTS

| JP | 3037156 | 2/1991 |
|---|---|---|
| WO | WO-91/10634 | 7/1991 |
| WO | WO-94/13584 | 6/1994 |
| WO | WO-94/29408 | 12/1994 |
| WO | WO-95/19222 | 7/1995 |
| WO | WO-03/102000 | 12/2003 |

OTHER PUBLICATIONS

Astles, PC et al., Selective endothelin A receptor ligands. 1. Discovery and structure-activity of 2,4-disubstituted benzoic acid derivatives, *Eur. J. Med. Chem.*, vol. 32 1997, 409-423.

Sisco, Scott W. et al., Directional Cyclooligomers via Alkyene Metathesis, *J. Am. Chem. Soc.*, vol. 134 2012, 9914-9917.

"JP3037156 Translation", *Detailed Description and Claims*, 5 pages, 2000.

Deng, Hexiang et al., Large-Pore Apertures in a Series of Metal-Organic Frameworks, *Science,* vol. 336 May 25, 2012, 1018-1023.

Fasina, Tolulope M. et al., Synthesis, optical properties, crystal structures and phase behaviour of symmetric, conjugated ethnylarene-based rigid rods with terminal carboxylate groups, *J. Mater. Chem.*, vol. 15 2005, 690-697.

Gadzikwa, Tendai et al., Ligand-elaboration as a strategy for engendering structural diversity in porous metal-organic framework compounds, *Chem Comm.* 2008, 3672-3674.

Kley, Christopher S. et al., Highly Adaptable Two-Dimensional Metal-Organic Coordination Networks on Metal Surfaces, *J. Am. Chem. Soc.*, vol. 134 2012, 6072-6075.

Matsubara, Hiroshi et al., Syntheses of Novel Fullerene Tweezers and Their Supramolecular Inclusion Complex of $C_{60}$, *Chemistry Letters* 1998, 1099-1100.

Nie, Xiaoping et al., Synthesis and Self-Assembling Properties of Diacetylene-Containing Glycolipids, *J. Org. Chem.*, vol. 71 2006, 4734-4741.

Pham, Bich Tram Nguyen et al., Novel Luminescent Metal-Organic Frameworks $[Eu_2L_3(DMSO)_2(MeOH)_2]$—$2DMSO$—$3H_2O$ and $[Zn_2L_2(DMSO)_2]$—$1.6H_2O$ (L=4,4'-Ethyne-1,2-diyldibenzoate), *Inorg. Chem.*, vol. 47 2008, 6329-6335.

Wendeborn, Helmut et al., Stückigmachen, Einleitung, *Ullmanns Encyklopädie der Technischen Chemie* vol. 2, Issue 4 1972, 313-314.

English Machine Translation of "Stückigmachen, Einleitung, *Ullmanns Encyklopädie der Technischen Chemie* vol. 2 Issue 4 1972, 313-314," 3 pages.

ACETYLENE BRIDGED LINKERS AND METAL-ORGANIC FRAMEWORKS (MOFS) PRODUCED THEREOF

CROSS-REFERENCE TO RELATED APPLICATIONS

This application claims the benefit of priority under 35 U.S.C. §119(a) to Indian Application No. 12/003897/CHENP, filed Sep. 19, 2012, the entire content of which is incorporated herein by reference in its entirety.

TECHNICAL FIELD

The present invention relates to acetylene bridged linkers, metal-organic frameworks produced thereof, processes for producing the linkers and the MOFs and their use.

BACKGROUND

Metal-organic frameworks are known. They are, in particular, distinguished by their porosity and can frequently be employed in applications comparable to those which are known for inorganic zeolites.

Metal-organic frameworks usually comprise an at least bidentate organic compound which is coordinated to a metal ion and joins at least two metal ions in a bridging fashion and, thus, together with the metal ions represents the skeleton of the metal-organic framework.

A suitable choice of metal and/or organic compound makes it possible to optimize the framework for the desired field of application. Here, for example, the choice of organic compound can have an influence on the pore distribution. Furthermore, the metal can make a contribution in adsorption processes.

A number of MOFs have been reported to exhibit a good adsorption/desorption behavior of economically interesting gases, e.g. methane and hydrogen.

Thus, there is an on-going task to provide porous materials exhibiting high surface area along with high heat of adsorption to pave the way into a sustainable hydrogen economy.

MOFs with magnesium as metal and phenylene based dihydroxy-dicarboxylic acids have been reported in Science 336 (2012) p. 1018-1023. The linkers differ in the number of phenylene rings that are attached to each other starting with 2,5-dihydroxyterephthalic acid IRMOF-74-I and ending with dihydroxy-dibenzoic acid groups that are separated by nine eventually substituted phenylene rings (IRMOF-74-XI). The BET surface areas for the series ranging from IRMOF-74-I to IRMOF-74-XI were found to be 1350, 2510, 2440, 2480, 2230, 1600, 1800, 1920, and 1760 m$^2$/g, respectively.

The Mg-MOF structure exhibits a very high affinity towards hydrogen, expressed by means of a heat of adsorption of hydrogen for IR-MOF74-II [Mg$_2$(4-(4-carboxy-3-hydroxy-phenyl)-2-hydroxy-benzoic acid)] at around 10 kJ/mol at 77K, values that are much higher compared to current best in class hydrogen storage material MOF177 (~5 kJ/mol).

Other dihydroxy-dicarboxylic acids with connecting groups other than phenylene are rarely known. An acetylene bridged compound comprising carboxy-hydroxy-phenyl end groups is known (CAS Registry Number 1348610-42-3). However, in this compound, the carboxylic groups are in meta-position and the hydroxylic groups are in para-position relating to the acetylene group.

Symmetrical diarylacetylenes are disclosed in a generic matter in DE 39 36 297 (U.S. Pat. No. 5,185,454 and EP 425 930, respectively) and WO 91/10634.

4,4'-Ethyne-1,2-diyldibenzoate, i.e. a compound without substituents at the aromatic rings, is reported in Inorganic Chemistry 2008, 47, 6329-6335.

The synthesis of another compound without substituents at the aromatic rings, i.e. 4,4'-di-(1,4,buta-1,3-diynyl) benzoic acid and its use in two-dimensional metal-organic coordination networks is described in J. Am. Chem. Soc. 2012, 134, 6072-6075. Therein, reference is made to syntheses of eventually substituted ethynylarenes: Chem. Lett. 1998, 1099-1100; J. Mater. Chem. 2005, 15, 690-697; and J. Org. Chem. 2006, 71, 4734-4741.

A series of 4,4'-ethynylenedibenzoic acids, their preparation and use as ligands in MOFs are described in Chem. Commun. 2008, 3672-3674.

SUMMARY

Aspects of a first embodiment are directed to a compound derived from a general structure (GS)

wherein R1 and R2 are independently selected from H, Bn, or CH$_3$; and wherein R: is chosen from carbons and/or hydrocarbons; has a C$_n$ symmetry with n≥2; and comprises at least one acetylene group.

In a second embodiment, the compound of the first embodiment is modified, wherein R=—(C≡C)$_a$— with a=1 to 5, having the general formula (GS-a)

and mixtures thereof.

In a third embodiment, the compound of the first and second embodiment is modified, wherein a=1, having the general formula (GS-I):

A fourth embodiment is directed to a compound of the general structure wherein R3=Si(CH$_3$)$_3$ or H.

A fifth embodiment is directed to a metal-organic framework comprising at least one compound according to the first through third embodiments as a linker, wherein R1=R2=H, coordinated to at least one metal ion.

In a sixth embodiment the metal-organic framework of the fifth embodiment is modified, wherein the metal is magnesium.

A seventh embodiment is directed to the production of metal-organic frameworks, wherein at least one compound according to embodiments 1 through 4 is used as a linker.

An eighth embodiment is directed to a method of adsorbing, storing and/or releasing at least one gas in the metal-organic framework of embodiment 5.

In a ninth embodiment, the method of the eighth embodiment is modified, wherein the gas is a methane-containing mixture or methane.

In a tenth embodiment, the method of eighth embodiment is modified, wherein the gas is hydrogen.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

Provided are metal-organic frameworks with an enhanced ability to adsorb and desorb high amounts of gases, in particular methane or hydrogen.

Further provided are metal-organic frameworks with a high porosity and, thus, a high inner surface, and compounds that might serve as linkers for said metal-organic frameworks.

According to embodiments of a first aspect of the present invention, provided are compounds which are derived from the general structure (GS)

wherein R1 and R2 are independently selected from H, Bn or CH$_3$; and
wherein R
is chosen from carbons and/or hydrocarbons;
has a C$_n$ symmetry with n≥2; and
comprises at least one acetylene group.

With respect to the terms used in this disclosure, the following definitions are provided.

As used herein, the term "derive" means that the benzene rings can be present in protonated form, partially deprotonated or completely deprotonated form. Furthermore, in one or more embodiments, the benzene rings can comprise a substituent or a plurality of independent substituents. Examples of such substituents are OH, NH$_2$, OCH$_3$, linear and/or branched C1 to C10 alkyl, NH(CH$_3$), N(CH$_3$)$_2$, CN and halides. However, in specific embodiments, the benzene rings are present in their protonated form, i.e. each benzene ring comprising three hydrogen atoms directly bound to the ring.

As used herein, the term "carbon" means a biradical rest consisting of carbon atoms. In one or more embodiments, a carbon comprises 1 to 5 acetylene units connected to each other with the structure (C≡C)$_a$.

As used herein, the term "hydrocarbon" means a biradical rest derived from linear or branched or cyclic saturated alkanes; linear or branched or cyclic monounsaturated alkenes and/or linear or branched polyunsaturated alka-polyenes and/or nonsubstituted, partially or totally substituted phenylenes.

According to one or more embodiments, R also comprises combinations of one or more carbons and one or more hydrocarbons.

As used herein, the term "C$_n$ symmetry" means that group R is symmetrical with regard to an n-fold axis. As used herein, the term "axis" refers to part of the paper plane and connects the two eventually substituted hydroxy benzoic acid end groups.

In one or more embodiments, the compounds are of the general structure GS wherein R=—(C≡C)$_a$— with a=1 to 5 having the general formula (GS-a)

and mixtures thereof.

In specific embodiments, the compounds are of the general structure GS-a wherein a=1:

(GS-1)

In very specific embodiments, the compounds are of the structure GS-1 with R1=R2=H, i.e. compounds of the structure I:

I

In other specific embodiments, the compounds are of the structure GS-a with a=2 and R1=R2=H, i.e. compounds of the structure II:

II

A second aspect of the present invention is directed to a method to produce compounds of the general structure GS.

In one or more embodiments, the method is directed to a method to produce compounds of the general structure GS-a wherein a=1:

(GS-1)

In other embodiments, the method is directed to a method to produce compounds of the structure GS-1 with R1=R2=H, i.e. compounds of the structure I:

I

Figure 1:
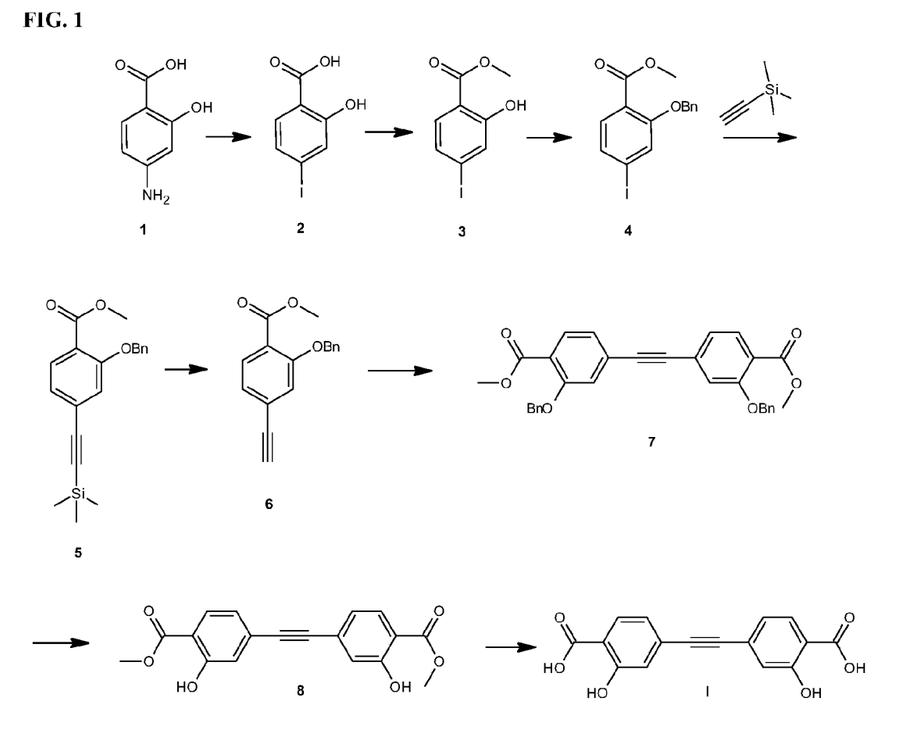
FIG. 1 depicts a chemical scheme for the synthesis of a compound according to the Examples.

A scheme for the synthesis of Compound I is depicted in FIG. 1.

In specific embodiments, the method is directed to a method to produce compounds of the structure GS-a with a=2 and R1=R2=H, i.e. compounds of the structure II:

II

Figure 2:
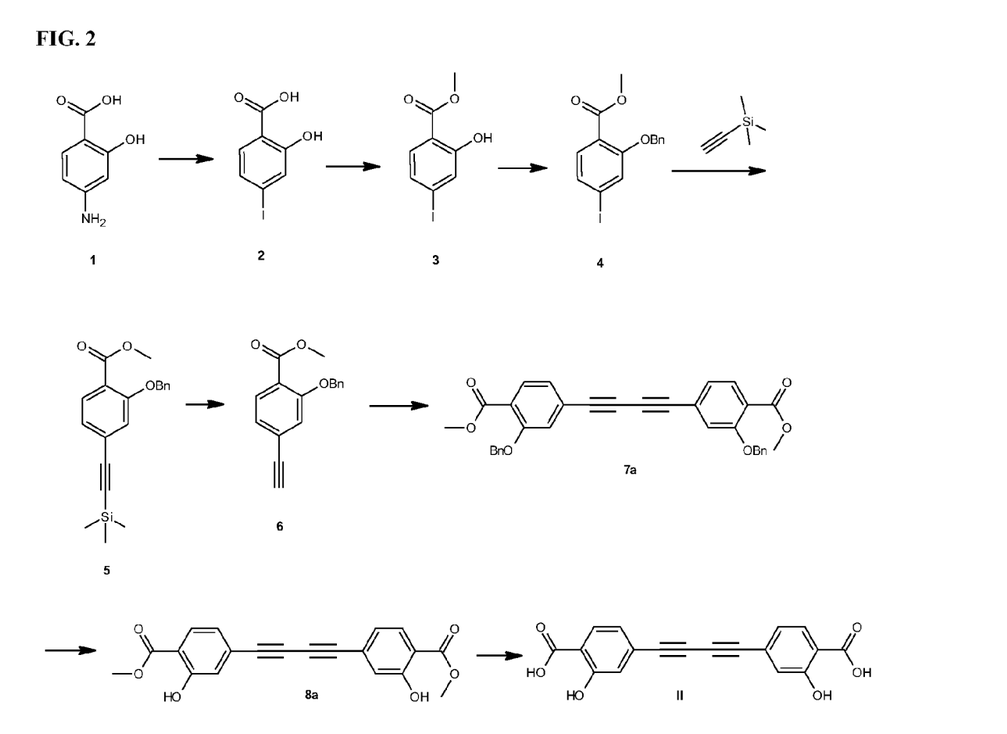
FIG. 2 depicts a chemical scheme for the synthesis of a compound according to the Examples.

A scheme for the synthesis of Compound II is depicted in FIG. 2.

Following the schematic synthesis of Compound I and Compound II, respectively, compounds with the following structure are yielded as intermediates:

wherein R3=Si(CH$_3$)$_3$ or H.

Embodiments of a further aspect of the present invention are directed to metal organic frameworks comprising at least one compound with the general structure GS with R1=R2=H as linker.

One or more embodiments are directed to metal organic frameworks comprising at least one compound of the general structure GS with R1=R2=H wherein R=—(C≡C)$_a$— with a=1 to 5 having the general formula and mixtures thereof.

Other embodiments are directed to metal organic frameworks comprising at least one compound of the general structure GS-a with R1=R2=H wherein a=1:

Specific embodiments are directed to metal organic frameworks comprising at least one compound of the structure GS-1 with R1=R2=H, i.e. compounds of the structure I:

Very specific embodiments are directed to metal organic frameworks comprising at least one compound of the structure GS-a with a=2 and R1=R2=H, i.e. compounds of the structure II:

According to one or more embodiments, the metal component in the framework selected from groups Ia, IIa, IIIa, IVa to VIIIa and Ib to VIb. Particular preference is given to Mg, Ca, Sr, Ba, Sc, Y, Ln, Ti, Zr, Hf, V, Nb, Ta, Cr, Mo, W, Mn, Re, Fe, Ro, Os, Co, Rh, Ir, Ni, Pd, Pt, Cu, Ag, Au, Zn, Cd, Hg, Al, Ga, Ln, Tl, Si, Ge, Sn, Pb, As, Sb and Bi, where Ln represents lanthanides. Lanthanides are La, Ce, Pr, Nd, Pm, Sm, En, Gd, Tb, Dy, Ho, Er, Tm, Yb.

In one or more embodiments, the metal organic framework comprises at least one metal. The metal organic framework can comprise only one metal, or can comprise two or more metals. As regards the ions of these elements, particular mention may be made of $Mg^{2+}$, $Ca^{2+}$, $Sr^{2+}$, $Ba^{2+}$, $Sc^{3+}$, $Y^{3+}$+, $Ln^{3+}$, $Ti^{4+}$, $Zr^{4+}$, $Hf^{4+}$, $V^{4+}$, $V^{3+}$, $V^{2+}$, $Nb^{3+}$, $Ta^{3+}$, $Cr^{3+}$, $Mo^{3+}$, $W^{3+}$, $Mn^{3+}$, $Mn^{2+}$, $Re^{3+}$, $Re^{2+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Rh^{2+}$, $Rh^+$, $Ir^{2+}$, $Ir^+$, $Ni^{2+}$, $Ni^+$, $Pd^{2+}$, $Pd^+$, $Pt^{2+}$, $Pt^+$, $Cu^{2+}$, $Cu^+$, $Ag^+$, $Au^+$, $Zn^{2+}$, $Cd^{2+}$, $Hg^{2+}$, $Al^{3+}$, $Ga^{3+}$, $In^{3+}$, $Tl^{3+}$, $Si^{4+}$, $Si^{2+}$, $Ge^{4+}$, $Ge^{2+}$, $Sn^{4+}$, $Sn^{2+}$, $Pb^{4+}$, $Pb^{2+}$, $As^{5+}$, $As^{3+}$, $As^+$, $Sb^{5+}$, $Sb^{3+}$, $Sb^+$, $Bi^{5+}$, $Bi^{3+}$ and $Bi^+$.

In one or more embodiments, the metal is selected from Mg, Al, Y, Sc, Zr, Ti, V, Cr, Mo, Fe, Co, Cu, Ni, Zn, Ln. In specific embodiments, the metal is selected from Al, Mg, Fe, Cu and Zn. In very specific embodiments, the metal comprises Mg.

According to one or more embodiments, the inner surfaces of the metal-organic frameworks are determined by methods that are known to one skilled in the art. In particular, these methods are the multipoint determination of the BET surface area by means of nitrogen adsorption at 77 K according to DIN 66131 and the determination of the surface area according to Langmuir.

In one or more embodiments, the inventive metal-organic frameworks exhibit surprisingly high surfaces. According to one or more embodiments, the surfaces of the metal-organic frameworks of the present invention are 1000 m²/g (BET) or above. In other embodiments, the surfaces of the metal-organic frameworks are 2000 m²/g (BET) or above, even more specifically 2500 m²/g (BET) or above. In very specific embodiments, the surfaces of the metal-organic frameworks of the present invention are 3000 m²/g (BET) or above.

Exemplarily, in one or more embodiments, an metal-organic framework (Example 3 in the Examples Section) exhibits a much higher surface area when compared to the phenylene based metal-organic frameworks of the state of the art (Comparative Examples 1 and 2): the surfaces of Example 1 are 3482 m²/g (BET) and 5092 m²/g (Langmuir), respectively.

The respective areas of the comparative examples are 1133 m²/g (BET) and 1535 m²/g (Langmuir) [Comparative Example 1] and 2469 m²/g (BET) and 3309 m²/g (Langmuir) [Comparative Example 2].

A further aspect of the present invention is directed to a method for the production of metal organic frameworks wherein at least one compound with the general structure GS with R1=R2=H is used as linker.

One or more embodiments are directed to method for the production of metal organic frameworks wherein at least one compound of the general structure GS with R1=R2=H wherein R=—(C≡C)$_a$— with a=1 to 5 having the general formula and mixtures thereof is used as linker.

Other embodiments are directed to a method for the production of metal organic frameworks wherein at least one compound of the general structure GS-a with R1=R2=H wherein a=1:

is used as linker.

Specific embodiments are directed to a method for the production of metal organic frameworks wherein at least one compound of the structure GS-1 with R1=R2=H, i.e. compounds of the structure I:

is used as a linker.

Very specific embodiments are directed to a method for the production of metal organic frameworks wherein at least one compound of the structure GS-a with a=2 and R1=R2=H, i.e. compounds of the structure II:

is used as a linker.

In one or more embodiments, the process for preparing a framework according to the invention comprises, as step (a), reaction of a reaction solution comprising a metal salt corresponding to the at least one metal ion and at least one compound with the general structure (GS) and also a solvent at a temperature in the range from 80° C. to 180° C. for at least 1 hour and (b) isolation of the precipitated solid.

In one or more embodiments, the reaction is carried out with stirring for at least part of the time, in particular at the beginning of the reaction.

In one or more embodiments, a metal salt is used as a starting compound. The initial concentration of this metal salt in the reaction mixture is in the range from 0.05 mol/l to 1.5 mol/l. In other embodiments, the initial concentration is in the range from 0.08 mol/l to 0.8 mol/l, even more specifically in the range from 0.1 mol/l to 0.5 mol/l. In specific embodiments, the initial concentration is in the range from 0.15 mol/l to 0.3 mol/l.

Furthermore, in one or more embodiments, the ratio of the initial molar amount of compounds with the general structure (GS) used to the initial molar amount of metal salt used, based on the metal, is in the range from 1:5 to 1:1. This means that according to one or more embodiments, the metal is used at least equimolar when compared to the linker; in specific embodiments, the metal is used in an excess. In other embodiments, the ratio is in the range from 1:4 to 1:2, more specifically in the range from 1:3.5 to 1:2.5.

In one or more embodiments, the reaction mixture for step (a) of the process of the invention for preparing the framework of the invention further comprises a solvent.

The solvent has to be suitable for at least partly dissolving the starting materials used. In addition, the solvent has to be selected in such a way that the required temperature range can be adhered to.

In one or more embodiments, the reaction in the process for preparing the material is thus carried out in the presence of a solvent. It is possible here to use solvothermal conditions. As used herein, the term "thermal" refers to a preparative process in which the reaction is carried out in a pressure vessel with the vessel closed during the reaction and elevated temperature being applied so that a pressure is built up within the reaction medium in the pressure vessel as a result of the vapor pressure of the solvent present. The desired reaction temperature can, if appropriate, be achieved in this way.

In one or more embodiments, the reaction is carried out in a water-comprising medium and likewise not under solvothermal conditions.

In one or more embodiments, the reaction is carried out at a pressure of not more than 2 bar (absolute). However, in other embodiments, the pressure is not more than 1230 mbar (absolute). In specific embodiments, the reaction takes place at atmospheric pressure. However, it is possible here for slightly superatmospheric or subatmospheric pressure to occur due to the apparatus. As used herein, the term "atmospheric pressure" therefore refers to a pressure range given by the actual prevailing atmospheric pressure±150 mbar.

In one or more embodiments, the reaction takes place in the temperature range from 80° C. to 180° C., more specifically in the range from 100° C. to 150° C. In other embodiments, the temperature is in the range from 105° C. to 140° C. In specific embodiments, the temperature is in the range from 110° C. to 125° C.

In one or more embodiments, the reaction solution further comprises a base. This serves, in particular, for making the acid readily soluble when an acid is used. The use of an organic solvent frequently makes it unnecessary to use such a base. Nevertheless, the solvent for the process of the invention can be selected so that it has a basic reaction, but this is not absolutely necessary for carrying out the process of the invention.

It is likewise possible to use a base. However, in one or more embodiments, no additional base is added.

Furthermore, in one or more embodiments, it is advantageous for the reaction to take place with stirring, which is also advantageous in the case of a scale-up.

In one or more embodiments, the organic solvent is preferably a $C_{1-6}$-alkanol, dimethyl sulfoxide (DMSO), N,N-dimethylformamide (DMF), N,N-diethylformamide (DEF), N,N-dimethylacetamide (DMAc), acetonitrile, toluene, dioxane, benzene, chlorobenzene, methyl ethyl ketone (MEK), pyridine, tetrahydrofuran (THF), ethyl acetate, halogenated or unhalogenated $C_{1-200}$ alkane, sulfolane, glycol, N-methylpyrrolidone (NMP), gamma-butyrolactone, alicyclic alcohols such as cyclohexanol, ketones such as acetone or acetylacetone, cyclic ketones, such as cyclohexanone, sulfolene or mixtures thereof.

As used herein, a $C_{1-6}$-alkanol is an alcohol having from 1 to 6 carbon atoms. Examples are methanol, ethanol, n-propanol, i-propanol, n-butanol, i-butanol, t-butanol, pentanol, hexanol and mixtures thereof.

As used herein, a halogenated or unhalogenated $C_{1-200}$-alkane is an alkane having from 1 to 200 carbon atoms in which one or more, up to all hydrogen atoms can or may be replaced by halogen, preferably chlorine or fluorine, in particular chlorine. Examples of this are chloroform, dichloromethane, tetrachloromethane, dichloroethane, hexane, heptane, octane, and mixtures thereof.

As used herein, the term "solvent" refers to pure solvents and mixtures of different solvents.

In one or more embodiments, solvents are a $C_{1-3}$-alkanols. In one or more embodiments, the solvent is ethanol.

In other embodiments, the solvents are selected from DMF, DEF, DMAc and NMP. In specific embodiments, the solvent is DMF.

In still further embodiments, solvents are mixtures of DMF, ethanol and water.

In one or more embodiments, the composition of these DMF-ethanol-water mixtures is a (DMF):b (ethanol):c (water) with a, b, and c being the respective volumes of the particular solvent whereas 'a' is in the range of from 220 ml to 330 ml, 'b' is in the range of from 5 ml to 80 ml and 'c' is in the range of from 5 to 40 ml, provided that a+b+c=340 ml. Other volumes can be calculated accordingly.

In one or more embodiments, step (a) of the process of the invention for preparing the framework is carried out for at least 1 hour; in other embodiments, for at least 3 hours. In specific embodiments, the reaction is carried out for at least 6 hours, more specifically at least 12 hours, even more specifically at least 18 hours.

In one or more embodiments, the process of the invention comprises the step (b), isolation of the precipitated solid.

As a result of step (a) of the preparative process of the invention, the framework precipitates from the reaction mixture as a solid. It can be isolated by methods known in the prior art, e.g. filtration or the like.

In one of more embodiments, the metal-organic framework of the invention can be present in powder form or as agglomerate.

In one or more embodiments, the porous metal-organic framework of the invention can be used as such in powder form or is converted into a shaped body.

In one or more embodiments, the porous metal-organic framework of the invention is present as powder.

Other embodiments of the invention, therefore, are directed to a shaped body comprising the porous metal-organic framework of the invention.

The production of shaped bodies from metal-organic frameworks is described, for example, in WO-A 03/102000.

Specific processes for producing shaped bodies are extrusion or tableting. In the production of shaped bodies, it is possible to add further materials such as binders, lubricants or other additives which are added during the production process. It is likewise conceivable for the framework to comprise further constituents, for example adsorbents such as activated carbon or the like.

The possible geometries of the shaped bodies are essentially not subject to any restrictions. For example, possible shapes are, inter alia, pellets such as disk-shaped pellets, pills, spheres, granules, extrudates such as rods, honeycombs, grids or hollow bodies.

To produce the shaped bodies, it is in principle possible to employ all suitable methods. In particular, the following processes are used:

kneading/pan milling of the framework either alone or together with at least one binder and/or at least one pasting agent and/or at least one template compound to give a mixture; shaping of the resulting mixture by means of at least one suitable method such as extrusion; optionally washing and/or drying and/or calcination of the extrudate; optionally finishing treatment.

tableting together with at least one binder and/or other auxiliaries.

application of the framework to at least one optionally porous support material. The material obtained can then be processed further by the above-described method to give a shaped body.

application of the framework to at least one optionally porous substrate

Kneading/pan milling and shaping can be carried out by any suitable method, for example as described in Ullmanns Enzyklopädie der Technischen Chemie, 4th edition, Volume 2, p. 313 ff. (1972).

For example, the kneading/pan milling and/or shaping can be carried out by means of a piston press, roller press in the presence or absence of at least one binder, compounding, pelletization, tableting, extrusion, coextrusion, foaming, spinning, coating, granulation, preferably spray granulation, spraying, spray drying or a combination of two or more of these methods.

Very particular preference is given to producing pellets and/or tablets.

In one or more embodiments, the kneading and/or shaping can be carried out at elevated temperatures, for example in the range from room temperature to 300° C., and/or under superatmospheric pressure, for example in the range from atmospheric pressure to a few hundred bar, and/or in a protective gas atmosphere, for example in the presence of at least one noble gas, nitrogen or a mixture of two or more thereof.

The kneading and/or shaping is, in a further embodiment, carried out with addition of at least one binder, with the binder used basically being able to be any chemical compound which ensures the desired viscosity for the kneading and/or shaping of the composition to be kneaded and/or shaped. Accordingly, binders can, for the purposes of the present invention, be either viscosity-increasing or viscosity-reducing compounds.

In one or more embodiments, the binders are, for example, inter alia aluminum oxide or binders comprising aluminum oxide, as are described, for example, in WO 94/29408, silicon dioxide as described, for example, in EP 0 592 050 A1, mixtures of silicon dioxide and aluminum oxide as are described, for example, in WO 94/13584, clay minerals as are described, for example, in JP 03-037156 A, for example montmorillonite, kaolin, bentonite, halloysite, dickite, nacrite and anauxite, alkoxysilanes as are described, for example, in EP 0 102 544 B1, for example tetraalkoxysilanes such as tetramethoxysilane, tetraethoxysilane, tetrapropoxysilane, tetrabutoxysilane, or for example trialkoxysilanes such as trimethoxysilane, triethoxysilane, tripropoxysilane, tributoxysilane, alkoxytitanates, for example tetraalkoxytitanates such as tetramethoxytitanate, tetraethoxytitanate, tetrapropoxytitanate, tetrabutoxytitanate, or for example trialkoxytitanates such as trimethoxytitanate, triethoxytitanate, tripropoxytitanate, tributoxytitanate, alkoxyzirconates, for example tetraalkoxyzirconates such as tetramethoxyzirconate, tetraethoxyzirconate, tetrapropoxyzirconate, tetrabutoxyzirconate, or for example trialkoxyzirconates such as trimethoxyzirconate, triethoxyzirconate, tripropoxyzirconate, tributoxyzirconate, silica soles, amphiphilic substances and/or graphites.

As viscosity-increasing compound, it is, for example, also possible to use, if appropriate, in addition to the abovementioned compounds, an organic compound and/or a hydrophilic polymer such as, for example, cellulose or a cellulose derivative such as methylcellulose and/or a polyacrylate and/or a polymethacrylate and/or a polyvinyl alcohol and/or a polyvinylpyrrolidone and/or a polyisobutene and/or a polytetrahydrofuran and/or a polyethylene oxide.

As pasting agent, it is possible to use, inter alia, water or at least one alcohol such as, for example: a monoalcohol having from 1 to 4 carbon atoms, for example methanol, ethanol, n-propanol, isopropanol, 1-butanol, 2-butanol, 2-methyl-1-propanol or 2-methyl-2-propanol, or a mixture of water and at least one of the alcohols mentioned or a polyhydric alcohol such as a glycol, preferably a water-miscible polyhydric alcohol, either alone or as a mixture with water and/or at least one of the monohydric alcohols mentioned.

Further additives which can be used for kneading and/or shaping are, inter alia, amines or amine derivatives such as tetraalkylammonium compounds or amino alcohols and carbonate-comprising compounds such as calcium carbonate. Such further additives are described, for instance, in EP 0 389 041 A1, EP 0 200 260 A1 or WO 95/19222.

The order of the additives such as template compound, binder, pasting agent, viscosity-increasing substance during shaping and kneading is in principle not critical.

In a further embodiment, the shaped body obtained by kneading and/or shaping is subjected to at least one drying step which is generally carried out at a temperature in the range from 25 to 500° C., or in the range from 50 to 500° C. and specifically in the range from 100 to 350° C. It is likewise possible to carry out drying under reduced pressure or under a protective gas atmosphere or by spray drying.

In a specific embodiment, at least one of the compounds added as additives is at least partly removed from the shaped body during this drying process.

The metal-organic framework of the invention and also the shaped bodies of the invention are suitable for storage of a gas.

A further aspect of the present invention is directed to a method for adsorbing, storing and/or releasing at least one gas by use of the metal-organic framework of the invention.

A specific gas is a methane-containing mixture or methane. Another specific gas is hydrogen. A further specific gas is carbon dioxide ($CO_2$).

Likewise, a further aspect of the present invention is directed to a method of storing a gas, which comprises the step of bringing the gas into contact with a framework according to the invention or a shaped body according to the invention.

Methane or methane-containing gases are particularly suitable for this storage.

Hydrogen is particularly suitable for this storage.

Carbon dioxide is also particularly suitable for this storage.

In addition, the framework of the invention or the shaped body of the invention is suitable for separating a gas from a gas mixture.

A further aspect of the present invention is directed to the use of a framework according to the invention or a shaped body according to the invention for separating a gas from a gas mixture.

Likewise, a further aspect of the present invention is directed to a method of separating a gas from a gas mixture, which comprises the step: bringing a framework according to the invention or a shaped body according to the invention into contact with the gas mixture.

The gas mixture is, in particular, a gas mixture comprising methane and other gases. Here, in one or more embodiments, methane is removed from the gas mixture.

Furthermore, the gas mixture can be a mixture comprising methane and water. Preference is given to removing gaseous water from the gas mixture. The gas mixture can be, for example, water-comprising natural gas.

Likewise, the gas mixture can be a gas mixture comprising hydrogen.

Likewise, the gas mixture can be a gas mixture comprising carbon dioxide.

The present invention is illustrated by means of the figures and the examples below.

FIG. 1 shows a scheme of the synthesis of 4-[2-(4-carboxy-3-hydroxy-phenyl)ethynyl]-2-hydroxy-benzoic acid (Compound I)

FIG. 2 shows a scheme of the of 4-[4-(4-carboxy-3-hydroxy-phenyl) buta-1,3-diinyl]-2-hydroxy-benzoic acid (Compound II)

Figure 3:
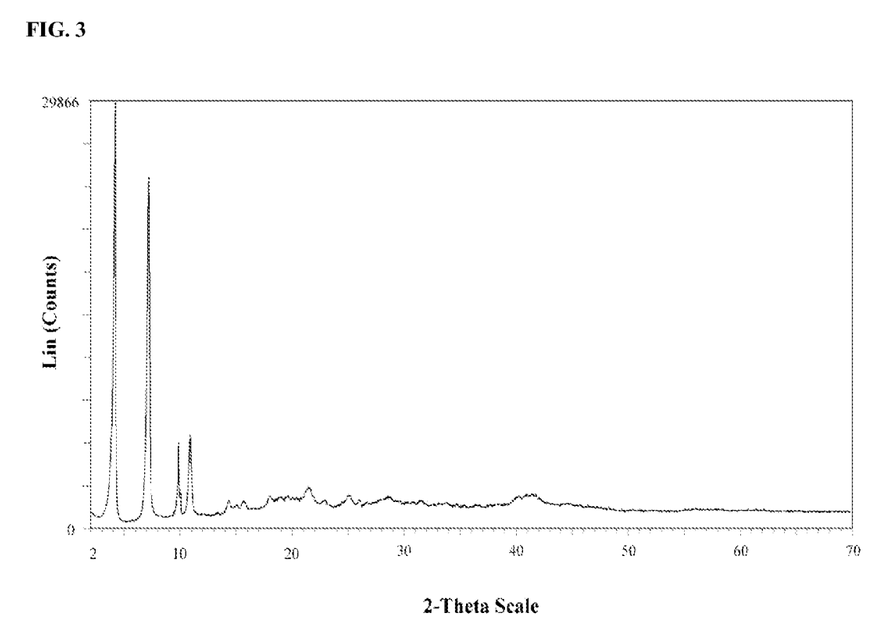
FIG. 3 depicts the XRD Pattern of the framework according to one or more embodiments.

FIG. 3 shows the XRD Pattern of the framework (Mg—Compound I) as per Example 3.

The respective list of reflexes can be found here (corrected):

| Angle 2-Theta ° | d value Angstrom | Intensity Count | Intensity % % |
|---|---|---|---|
| 4.099 | 21.54 | 29432 | 100 |
| 7.099 | 12.44 | 24216 | 82.3 |
| 9.779 | 9.04 | 5264 | 17.9 |
| 9.922 | 8.91 | 1978 | 6.7 |
| 10.815 | 8.17 | 5766 | 19.6 |
| 13.153 | 6.73 | 195 | 0.7 |
| 14.263 | 6.2 | 969 | 3.3 |
| 15.039 | 5.89 | 582 | 2 |
| 15.607 | 5.67 | 843 | 2.9 |
| 17.963 | 4.93 | 1113 | 3.8 |
| 18.861 | 4.7 | 959 | 3.3 |
| 19.582 | 4.53 | 1054 | 3.6 |
| 21.408 | 4.15 | 1526 | 5.2 |
| 22.865 | 3.89 | 592 | 2 |
| 25.059 | 3.55 | 916 | 3.1 |
| 25.969 | 3.43 | 576 | 2 |
| 26.592 | 3.35 | 380 | 1.3 |
| 28.619 | 3.12 | 737 | 2.5 |
| 30.232 | 2.95 | 394 | 1.3 |
| 30.819 | 2.9 | 388 | 1.3 |
| 31.473 | 2.84 | 440 | 1.5 |
| 33.089 | 2.71 | 286 | 1 |
| 33.753 | 2.65 | 314 | 1.1 |

-continued

| Angle 2-Theta ° | d value Angstrom | Intensity Count | Intensity % % |
|---|---|---|---|
| 34.661 | 2.59 | 314 | 1.1 |
| 35.325 | 2.54 | 154 | 0.5 |
| 36.312 | 2.47 | 200 | 0.7 |
| 37.64 | 2.39 | 246 | 0.8 |
| 38.36 | 2.34 | 268 | 0.9 |
| 40.24 | 2.24 | 845 | 2.9 |
| 40.88 | 2.21 | 1011 | 3.4 |
| 41.422 | 2.18 | 1005 | 3.4 |

Figure 4:
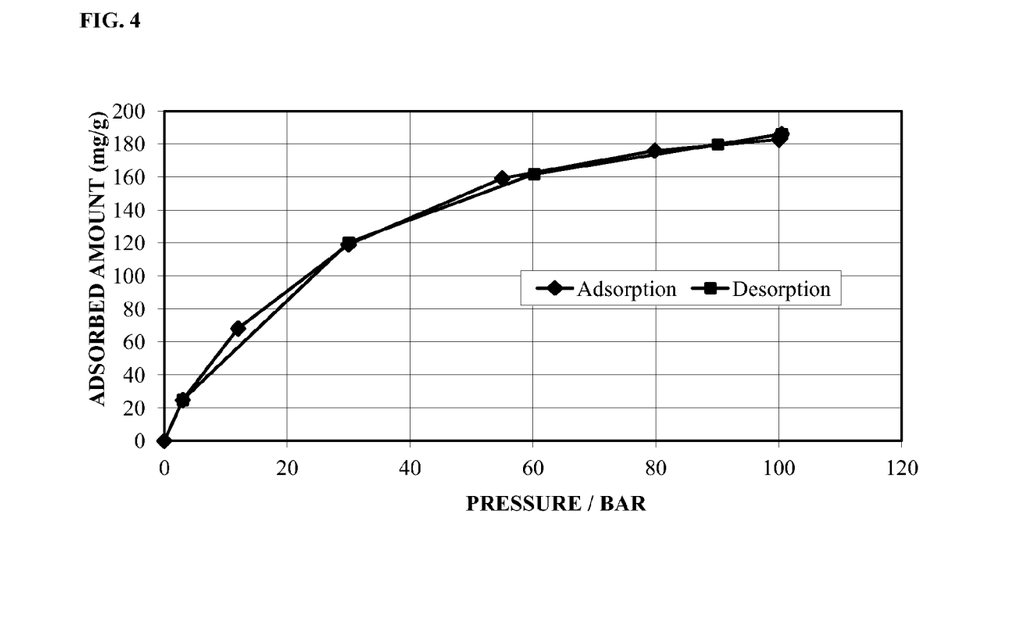
FIG. 4 shows the adsorption and desorption at ambient temperature for a metal-organic framework according to one or more embodiments.

FIG. 4 shows the adsorption and desorption at ambient temperature for a metal-organic framework (Mg—Compound I) as per Example 3. Here, the amount of adsorbed gas (methane) in mg per gram of framework is shown as a function of the absolute pressure p in bar. The excess methane uptake at ambient temperature and 100 bar is 18.3 wt %.

Figure 5:
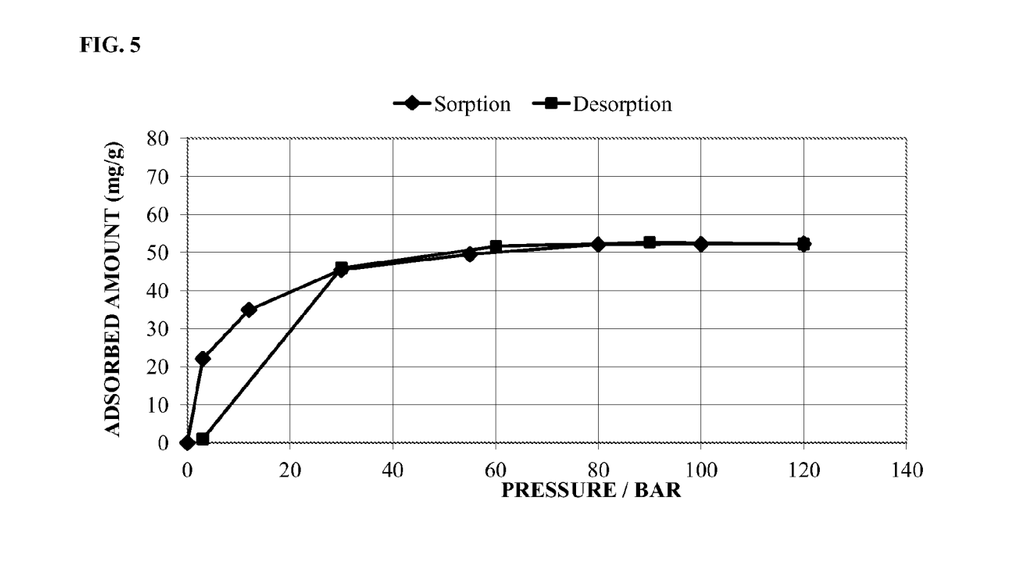
FIG. 5 shows the adsorption and desorption at 77 K for a metal-organic framework according to the Examples.

FIG. 5 shows the adsorption and desorption at 77 K for a metal-organic framework (Mg—Compound I) as per Example 3. Here, the amount of adsorbed gas (hydrogen) in mg per gram of framework is shown as a function of the absolute pressure p in bar. The excess hydrogen uptake at 77 K and 100 bar is 5.2 wt %.

Figure 6:
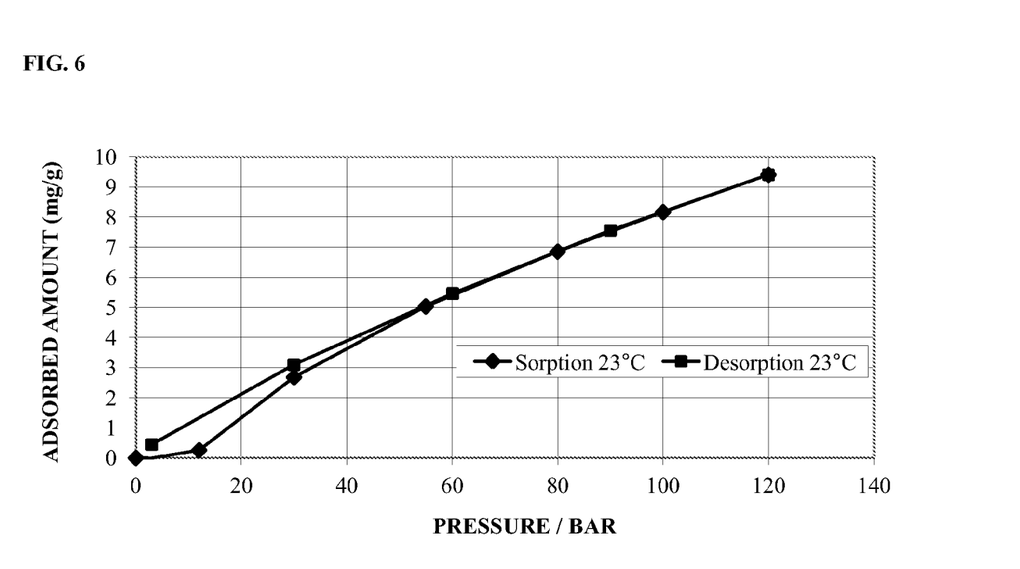
FIG. 6 shows the adsorption and desorption at ambient temperature for a metal-organic framework according to the Examples.

FIG. 6 shows the adsorption and desorption at ambient temperature for a metal-organic framework (Mg—Compound I) as per Example 3. Here, the amount of adsorbed gas (hydrogen) in mg per gram of framework is shown as a function of the absolute pressure p in bar. The excess hydrogen uptake at ambient temperature and 100 bar is 0.82 wt %.

The invention is now described with reference to the following examples.

EXAMPLES

Example 1

Synthesis of 4-[2-(4-carboxy-3-hydroxy-phenyl)ethynyl]-2-hydroxy-benzoic acid (I)

Synthesis of Compound 2

11.0 g (72.0 mmol) of 4-aminosalicylic acid (1) was taken in 110.0 ml 50% $H_2SO_4$ and cooled to −5° C. and stirred for 20 minutes. To this $NaNO_2$ solution (5.5 g, 80 mmol of $NaNO_2$ in 6.5 ml deionized water) was added drop wise maintaining temperature below 0° C. and stirred for 20 minutes. This diazonium salt solution was added drop wise to the freshly prepared CuI solution* at −5° C. After addition, temperature of the reaction mixture was raised to room temperature and then heated to 90° C. for 1 h. After completion of reaction, the reaction mixture was cooled to room temperature and filtered to obtain yellow solid which was washed with water and dried. This solid was dissolved in hot ethanol and filtered. The inorganic residue remained was washed with ethanol and the filtrate was evaporated to dryness under vacuum to obtain 16.0 g of crude Compound 2 as a brown solid.

*(CuI solution: 17.95 g (72.0 mmol) CuSO$_4$.5H$_2$O, 5.5 g (86.0 mmol) Cu-powder and 55.0 g (332.0 mmol) KI were taken in 100.0 ml deionized water. To this 100.0 ml 20% H$_2$SO$_4$ was added with constant stirring. Reaction mixture was allowed to stirred at room temperature for 1 h and then it was cooled to −5° C. CuI gets precipitated out as off-white solid.

The above solution of CuI is directly used for the preparation of Compound 2.

Yield: 84.6%

Analysis: $^1$H NMR (300 MHz, MeOD): δ 7.48 (d, 1H); 7.24 (d, 1H); 7.19 (dd, 1H). MS (m/z): 263 (M$^+$−H)

Synthesis of Compound 3

10.0 g (37.8 mmol) of Compound 2 was taken in 200.0 ml dry methanol. To this 11.5 ml (151.0 mmol) of SOCl$_2$ was added drop wise. Then the reaction mixture was refluxed for 10 h. After completion of reaction, the reaction mixture was cooled to room temperature and methanol was evaporated to dryness under vacuum to obtain 12.0 g crude product which was further purified by washing with minimum amount of methanol to obtain 5.2 g of Compound 3.

Yield: 50.0%

Analysis: $^1$H NMR (300 MHz, CDCl$_3$): δ 10.8 (s, 1H); 7.49 (d, 1H); 7.40 (d, 1H); 7.24 (dd, 1H); 3.9 (s, 3H). MS (m/z): 277 (M$^+$−H)

Synthesis of Compound 4

5.2 g (18.7 mmol) of Compound 3 and 16.0 g (37.4 mmol) of K$_2$CO$_3$ were taken in 40.0 ml acetonitrile. To this 2.4 ml (19.6 mmol) of benzyl bromide was added drop wise at RT. Then the reaction mixture was heated to 80° C. for 4 h. After completion of reaction, the reaction mixture was cooled to room temperature and filtered. The solid residue remained was repeatedly washed with ethyl acetate. Finally the filtrate was evaporated to dryness under vacuum to obtain 7.0 g of Compound 4 as dark brown oily liquid which solidifies on standing at room temperature.

Yield: 99.9%

Analysis: $^1$H NMR (300 MHz, CDCl$_3$): δ 7.47-7.41 (m, 3H); 7.39-7.31 (m, 5H); 5.1 (s, 2H); 3.9 (s, 3H). MS (m/z): 367 (M$^+$−H)

Synthesis of Compound 5

1.0 g (2.7 mmol) of Compound 4, 0.58 ml (4.1 mmol) of trimethylsilyl acetylene, 0.05 g (0.27 mmol) of copper iodide and 0.75 ml (5.4 mmol) of TEA were taken in 5.0 ml dioxane. The reaction system was degassed thoroughly. To this 0.95 g (0.135 mmol) of (PPH$_3$)$_2$PdCl$_2$ was added under inert atmosphere and the reaction was stirred for 1 h at room temperature. After completion of reaction, dioxane was evaporated to dryness. The residue remained was dissolved in chloroform and filtered through celite. The filtrate was evaporated to dryness to obtain crude product to which methanol was added. On addition of methanol, impurities precipitated out as solid which was filtered and remaining filtrate was evaporated under vacuum to obtain 0.9 g of Compound 5 as brown oily liquid.

Yield: 99.0%

Analysis: $^1$H NMR (300 MHz, CDCl$_3$): δ 7.6 (d, 1H); 7.33-7.30 (dd, 2H); 7.23-7.13 (m, 3H); 6.93-6.89 (m, 2H); 4.98 (s, 2H); 3.7 (s, 3H); 0.06 (s, 9H). MS (m/z): 339 (M$^+$+H)

Synthesis of Compound 6

0.2 g (0.6 mmol) of Compound 5 and 0.16 g (1.2 mmol) of K$_2$CO$_3$ were taken in 5.0 ml of methanol. The reaction was stirred at room temperature for 2 h. After completion of reaction, methanol was evaporated to dryness. Excess of water was added to the reaction mass and extracted with ethyl acetate. The ethyl acetate layer was evaporated to dryness to obtain 0.15 g of Compound 6.

Yield: 95.5%

Analysis: $^1$H NMR (300 MHz, CDCl$_3$): δ 7.65 (d, 1H); 7.39-7.35 (dd, 2H); 7.23-7.13 (m, 3H); 6.93-6.89 (m, 2H); 5.09 (s, 2H); 3.8 (s, 3H); 3.1 (s, 1H). MS (m/z): 267 (M$^+$+H)

Synthesis of Compound 7

0.6 g (1.6 mmol) of Compound 6, 0.65 g (2.4 mmol) of Compound 4, 0.031 g (0.16 mmol) of copper iodide and 0.45 ml (3.2 mmol) of TEA were taken in 10.0 ml dioxane. The reaction system was degassed thoroughly. To this 0.057 g (0.08 mmol) of (PPH$_3$)$_2$PdCl$_2$ was added under inert atmosphere and the reaction was stirred for 1 h at room temperature. After completion of reaction, dioxane was evaporated to dryness. The residue remained was dissolved in chloroform and filtered through celite. The filtrate was evaporated to dryness to obtain crude product. This was purified by combiflash silica gel column chromatography to get 0.5 g of Compound 7 as off white solid.

Yield: 45.5%

Analysis: $^1$H NMR (300 MHz, CDCl$_3$): δ 7.7 (d, 2H); 7.45 (dd, 4H); 7.38-7.24 (m, 6H); 7.16-7.07 (m, 4H); 5.11 (s, 4H); 3.9 (s, 6H). MS (m/z): 507 (M$^+$+H)

Synthesis of Compound 8

0.5 g of Compound 7 and was taken in 5.0 ml toluene. To this 1.0 ml of TFA was added drop wise till formation of clear solution. Reaction was stirred at room temperature for 16 h. After completion of reaction, toluene and TFA was evaporated to dryness to obtain crude oily residue. To this heptane was added and crude mass was stirred vigorously to obtain 0.15 g Compound 8 as off white solid. (% Y=47).

Yield: 46.5%

Analysis: $^1$H NMR (300 MHz, CDCl$_3$): δ 10.74 (s, 2H); 7.76 (d, 2H); 7.08 (d, 2H); 6.98-6.93 (dd, 2H); 3.8 (s, 6H). MS (m/z): 327 (M$^+$+H)

Synthesis of Compound I 0.15 g (0.4 mmol) of Compound 8 and 0.18 g (4.5 mmol) of NaOH were taken in 4.0 ml THF and 4.0 ml water. Reaction mixture was heated at 80° C. for 4 hrs. After completion of reaction, THF layer was evaporated and the remaining aqueous layer was acidified with dilute HCl. The solid precipitated out was filtered, washed with water and dried to obtain 0.1 g of crude Compound I as off white solid.

Yield: 76.9%

Analysis: $^1$H NMR (300 MHz, DMSO): δ 7.9-7.7 (m, 2H); 7.2-6.9 (m, 4H). $^{13}$C NMR (300 MHz, DMSO): δ 91.15; 114.35; 120.19; 122.76; 131.17; 161.16; 171.60. Melting point: >250° C.

Example 2

Synthesis of 4-[4-(4-carboxy-3-hydroxy-phenyl)buta-1,3-diinyl]-2-hydroxy-benzoic acid (II)

Synthesis of Compound 7A 5.0 g (18.77 mmol) of Compound 6, 0.35 g (1.87 mmol) of copper iodide and 3.1 ml (22.53 mmol) of TEA were taken in 50.0 ml THF. The reaction mass was stirred for 16 h at room temperature. After completion, water was added to quench the reaction and THF was evaporated. The aqueous layer was extracted with chloroform (2×50.0 ml). The combined organic layers was dried under sodium sulfate and concentrated to give 1.5 g of Compound 7A as yellow solid.

Yield: 15.15%

Analysis: $^1$H NMR (300 MHz, CDCl$_3$): δ 7.8 (d, 2H); 7.5 (dd, 4H); 7.45-7.21 (m, 6H); 7.16-7.07 (m, 4H); 5.2 (s, 4H); 3.9 (s, 6H). GCMS (m/z): 530 (M$^+$)

Synthesis of Compound 8A 3.5 g of Compound 7A and was taken in 35.0 ml toluene. To this 7.0 ml of TFA was added drop wise till formation of clear solution. Reaction was stirred at room temperature for 16 h. After completion of reaction, toluene and TFA was evaporated to dryness to obtain crude oily residue. To this heptane was added and crude mass was stirred vigorously to obtain 1.5 g Compound 8A as off white solid.

Yield: 71.4%

Analysis: $^1$H NMR (300 MHz, CDCl$_3$): δ 10.8 (s, 2H); 7.8 (d, 2H); 7.3 (d, 2H); 7.0 (dd, 2H); 4.0 (s, 6H). GCMS (m/z): 350 (M$^+$)

Synthesis of Compound II 1.4 g (4.00 mmol) of Compound 8A and 1.6 g (40.00 mmol) of NaOH were taken in 14.0 ml THF and 14.0 ml water. Reaction mixture was heated at 60° C. for 4 hrs. After completion of reaction, THF layer was evaporated and the remaining aqueous layer was acidified with dilute HCl. The solid precipitated out was filtered, washed with water and dried to obtain 1.2 g of Compound II as light yellow solid.

Yield: 94%

Analysis: $^1$H NMR (300 MHz, DMSO): δ 7.9-7.7 (m, 2H); 7.2-7.0 (m, 4H). $^{13}$C NMR (300 MHz, DMSO): δ 75.70; 82.24; 115.18; 121.12; 123.51; 127.03; 131.25; 161.04; 171.49. GCMS (m/z): 322 (M$^+$). Melting Point>250° C.

Example 3

Synthesis of Mg-MOF: [Mg$_2$(Compound I)]

To 225 ml DMF in a 500 ml flask under nitrogen atmosphere 2.4 g Mg(NO$_3$)$_2$×6 H$_2$O (9.375 mmol) and 0.85 g 4-[2-(4-carboxy-3-hydroxy-phenyl)ethynyl]-2-hydroxy-benzoic acid (2.85 mmol) were added under stiffing. To the obtained slightly yellow solution 15 ml Ethanol was added, followed by drop-wise addition of 15 ml distilled water. After stirring for 30 min at ambient temperature the reaction mixture was heated to 120° C. for 24 h under gentle reflux. After 30 min of heating the precipitation of solid material started. After cooling down to ambient temperature the mother liquor was separated via filtration on a glass frit under nitrogen atmosphere. The precipitate was washed twice with 20 ml DMF, twice with 20 ml dry Methanol and then transferred to a Soxhlett extractor and extracted with Methanol for 16 h. The received solid was dried at 50 mbar for 2 h at ambient temperature and 16 h at 130° C. After drying 0.78 g of an off-white solid was obtained (yield based on linker 79.6%).

The tamped density was found to be 260 g/L. The surface area was 3482 m$^2$/g (BET-method) and 5092 m$^2$/g (Langmuir method). The XRD pattern exhibits reflexes in the area typical for microporous materials (FIG. 3).

Example 4

Synthesis of Mg-MOF: [Mg$_2$(Compound II)]

To 300 ml DMF under nitrogen atmosphere 3.20 g Mg(NO$_3$)$_2$×6 H$_2$O (12.5 mmol) and 1.22 g 4-[4-(4-carboxy-3-hydroxy-phenyl)buta-1,3-diynyl]-2-hydroxy-benzoic acid (3.8 mmol) is added under stirring. To the obtained slightly yellow solution 30.0 ml Ethanol is added, followed by drop-wise addition of 10.0 ml distilled water. After stirring for 30 min at ambient temperature the reaction mixture is heated to 120° C. for 24 h under gentle reflux and stirring (100 RPM).

After cooling down to ambient temperature the mother liquor is separated via filtration on a glass frit under nitrogen atmosphere. The precipitate is washed twice with 20 ml DMF, twice with 20 ml of dry Methanol and then transferred to a Soxhlett extractor and extracted with Methanol for 16 h. The received solid is dried at 50 mbar for 2 h at ambient temperature and 16 h at 130° C.

Comparison Example 1

Synthesis of Mg-MOF:
[$Mg_2$(2,5-dihydroxyterephthalic acid)]
(IRMOF-74-I; commercial name: Basolite M74)

To 300 ml DMF under nitrogen atmosphere 3.20 g $Mg(NO_3)_2 \times 6\ H_2O$ (12.5 mmol) and 0.76 g 2,5-dihydroxyterephthalic acid (3.8 mmol) were added under stirring. To the obtained slightly yellow solution 20.0 ml Ethanol was added, followed by drop-wise addition of 20.0 ml distilled water. After stirring for 30 min at ambient temperature the reaction mixture was heated to 120° C. for 24 h under gentle reflux and stirring (100 RPM). After cooling down to ambient temperature the mother liquor was separated via filtration on a glass frit under nitrogen atmosphere. The precipitate was washed twice with 20 ml DMF, twice with 20 ml of dry Methanol and then transferred to a Soxhlett extractor and extracted with Methanol for 16 h. The received solid was dried at 50 mbar for 2 h at ambient temperature and 16 h at 130° C. After drying 1.00 g of an off-white solid was obtained (yield based on linker 107.5%).

The surface area was 1133 $m^2/g$ (BET-method) and 1535 $m^2/g$ (Langmuir method). The XRD pattern exhibits reflexes in the area typical for microporous materials.

Comparison Example 2

Synthesis of Mg-MOF: [$Mg_2$(4-(4-carboxy-3-hydroxy-phenyl)-2-hydroxy-benzoic acid)];
IR-MOF74-II To 1186 ml DMF under nitrogen atmosphere 12.67 g $Mg(NO_3)_2 \times 6\ H_2O$ (49.3 mmol) and 4.12 g 4-(4-carboxy-3-hydroxy-phenyl)-2-hydroxy-benzoic acid (15 mmol) were added under stiffing. To the obtained slightly yellow solution 79.3 ml Ethanol was added, followed by drop-wise addition of 79.3 ml distilled water. After stirring for 30 min at ambient temperature the reaction mixture was heated to 120° C. for 12 h under gentle reflux and stirring (130 RPM). After 60 min of heating, the precipitation of solid material started. After cooling down to ambient temperature the mother liquor was separated via filtration on a glass frit under nitrogen atmosphere. The precipitate was washed twice with 200 ml DMF, twice with 200 ml of dry Methanol and then transferred to a Soxhlett extractor and extracted with Methanol for 16 h. The received solid was dried at 0.2 mbar for 2 h at ambient temperature, 2 h at 60° C. and 16 h at 130° C. Further activation occurred via drying for 16 h at 0.01 bar. After activation 12.08 g of an off-white solid was obtained (yield based on linker 83.6%).

The tamped density was found to be 170 g/L. The surface area was 2469 $m^2/g$ (BET-method) and 3309 $m^2/g$ (Langmuir method). The XRD pattern exhibits reflexes in the area typical for microporous materials.

Comparative Examples 1 and 2 are described in Science 336 (2012) p. 1018-1023.

| | Tamped density [g/L] | Surface area (BET) [$m^2/g$] | Surface area (Langmuir) [$m^2/g$] | XRD pattern: Microporous material? |
|---|---|---|---|---|
| Example 3 | 260 | 3482 | 5092 | Yes |
| Comp. Ex. 1 | 480 | 1133 | 1535 | Yes |
| Comp. Ex. 2 | 170 | 2469 | 3309 | Yes |

All references, including publications, patent applications, and patents, cited herein are hereby incorporated by reference for all purposes to the same extent as if each reference were individually and specifically indicated to be incorporated by reference and were set forth in its entirety herein.

The use of the terms "a" and "an" and "the" and similar referents in the context of describing the materials and methods discussed herein (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the materials and methods and does not pose a limitation on the scope unless otherwise claimed. No language in the specification should be construed as indicating any non-claimed element as essential to the practice of the disclosed materials and methods.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A metal-organic framework comprising at least one linker coordinated to at least one metal ion, wherein the linker is a compound derived from the general structure (GS)

wherein R1=R2=H; and
wherein R
- is chosen from carbons and/or hydrocarbons,
- has a $C_n$ symmetry with n≥2, and comprises at least one acetylene group.

2. The metal-organic framework of claim 1, wherein the metal ion is magnesium.

3. A method comprising adsorbing, storing and/or releasing at least one gas in the metal-organic framework of claim 1.

4. The method of claim 3, wherein the gas is a methane-containing mixture or methane.

5. The method of claim 3, wherein the gas is hydrogen.

6. The metal-organic framework of claim 1,
wherein R=—(C≡C)$_a$— and a=1 to 5, such that the compound has a general structure (GS-a)

7. The metal-organic framework of claim 6, wherein the metal ion is magnesium.

8. The metal-organic framework of claim 6, wherein the compound has the general structure (GS-I)

9. The metal-organic framework of claim 8, wherein the metal ion is magnesium.

* * * * *